United States Patent [19]

Chiang et al.

[11] Patent Number: 4,713,333

[45] Date of Patent: Dec. 15, 1987

[54] IMMOBILIZATION OF BIOCATALYSTS ON GRANULAR DIATOMACEOUS EARTH

[75] Inventors: John P. Chiang, Elkhart; Oreste J. Lantero, Jr., Goshen, both of Ind.

[73] Assignee: Miles Laboratories, Inc., Elkhart, Ind.

[21] Appl. No.: 779,053

[22] Filed: Sep. 23, 1985

[51] Int. Cl.$^4$ .................... C12P 19/20; C12N 11/14
[52] U.S. Cl. .................................. 435/96; 435/176
[58] Field of Search ................................ 435/176, 96

[56] References Cited

U.S. PATENT DOCUMENTS

| | | | |
|---|---|---|---|
| 3,796,634 | 3/1974 | Haynes et al. | 435/176 X |
| 4,141,857 | 2/1979 | Levy et al. | 435/180 X |
| 4,292,199 | 9/1981 | Rohrbach et al. | 435/180 X |
| 4,438,196 | 3/1984 | Lantero, Jr. | 435/177 X |
| 4,581,338 | 4/1986 | Robertson et al. | 435/176 X |
| 4,665,028 | 5/1987 | Amotz | 435/174 |

OTHER PUBLICATIONS

Derwent Abstract, 80941A/45 of Japanese Pat. No. 53-113082, (Oct. 1978).

*Primary Examiner*—Lionel M. Shapiro
*Attorney, Agent, or Firm*—Jennifer L. Skord; Jerome L. Jeffers

[57] ABSTRACT

Disclosed is a process whereby enzymes are immobilized on granular diatomaceous earth. The process involves treating the diatomaceous earth with a polyamine compound having pendant amino groups to cause the polyamine to adhere to the diatomaceous earth leaving pendant amine groups free to react further. The free amine groups are derivatized by treatment with a difunctional compound having amine reactive moieties, so that free amine groups of an enzyme or enzymes can be covalently bound to the polyamine via the amine reactive compound.

19 Claims, No Drawings

0
IMMOBILIZATION OF BIOCATALYSTS ON GRANULAR DIATOMACEOUS EARTH

This invention involves an immobilized enzyme conjugate and a method of preparing such conjugate. More particularly, the enzyme is immobilized on a support of granular diatomaceous earth.

BACKGROUND OF THE INVENTION

Enzymes, which are proteinaceous in nature and are commonly water soluble behave as biocatalysts, regulating many of the chemical reactions which occur in living organisms. Enzymes may also be isolated and used in analytical, medical and industrial applications. For example, they are used in the preparation of food such as cheese and bread as well as in the preparation of alcoholic beverages.

Since enzymes are commonly water soluble as well as being generally unstable, they are subject to deactivation and are difficult to remove for reuse from solutions in which they are utilized. These difficulties lead to an increased cost in the use of enzymes in commercial scale operations due to the necessity for their frequent replacement. In order to reduce the high cost of enzyme replacement, various methods for immobilization (sometimes referred to as insolubilization) of enzymes prior to their use have been devised. This immobilization of the enzyme permits its reuse whereas it might otherwise undergo deactivation or be lost in the reaction medium in which it is used. These immobilized enzyme systems may be employed in various reactor systems, such as in packed columns and stirred tank reactors, depending on the nature of the substrate which is being biocatalytically reacted.

Several general methods as well as many modifications thereof have been described by which the immobilization of enzymes can be effected. For example, materials useful for immobilization of enzymes or cells containing enzymes are disclosed in U.K. Pat. No. 1,444,539. Preferably, the enzymes or cells are treated with a water miscible solvent, such as acetone, dried and then treated with polyethylenimine and glutaraldehyde to make shaped bodies of a water insoluble structure.

More particularly, in U.S. Pat. No. 3,796,634 there is disclosed an immobilization method which involves absorbing a polyamine onto the surface of colloidal sized particles. The polyamine is cross-linked with a conventional amine-reactive cross-linking agent, e.g. glutaraldehyde, and the resulting reaction product is treated with $NaBH_4$ to reduce the aldehyde groups and thereby prevent any covalent bonding between the aldehyde groups and the enzyme's amino group. Next, the enzyme is absorbed onto the treated surface of the particle at a pH such that the colloidal absorbant bears a net electric charge opposite that of the enzyme molecules so that ionic bonding aids other non-covalent bonding forces. This patent describes the absorbant particles as ranging in size from about 50 to about 20,000 angstroms, preferably from about 100 to 200 angstroms in diameter, with the absorbant material being activated charcoal, hydroxyapatite, alumina C gamma, and bentonite. This system depends on charge interactions for binding the enzyme to the treated particles. This type of bonding is less desirable than the formation of covalent linkages because ionic interactions are susceptible to the environmental conditions relative to this type of linkage such as pH, ionic strength and temperature.

Liu, et al disclose an immobilization method for lactase on granular carbon in *Biotechnol. Bioeng.* 17, 1695–1696, 1975 which involves absorbing p-aminophenol or 1-phenol-2-amino-4-sulfonic acid to the carbon. These absorbed compounds provide the amino groups with which glutaraldehyde reacts and in turn binds the enzyme. The amino group containing compounds mentioned are monomers which possess chemical and physical properties different from those of a polyamine such as polyethylenimine.

Another group of workers (Cho, et al, Immobilization of Enzymes on Activated Carbon: Properties of Immobilized Glucoamylase, Glucose Oxidase and Gluconolactonase, *Biotechnol. Bioeng.* 20, 1651–1665, 1978) have also immobilized enzymes on granular carbon by covalent attachment. In this process carbon is activated by a carbodiimide which can be displaced by an enzyme to form an enzyme-carbon complex.

U.S. Pat. No. 4,141,857 discloses a method for enzyme immobilization which involves treating an inorganic porous support material such as gamma-alumina having pore diameters of from about 100 to about 55,000 angstroms and a surface area of about 100 to 500 $m^2$ per gram with a solution of a water soluble polyamine and contacting the treated support material with a solution of a bifunctional monomeric material, e.g. glutaraldehyde. This treatment leaves the treated support material suitable for reaction with the enzyme so as to form covalent bonds between the enzyme and the pendant aldehyde groups. In Example II of this patent there is described the preparation of an immobilized enzyme conjugate by treating porous alumina spheres sequentially with solutions of polyethylenimine, glutaraldehyde and glucoamylase.

In U.S. Pat. No. 4,438,196 there is disclosed a process whereby enzymes are immobilized on activated granular carbon. The process involves treating the carbon with a polyamine compound having pendant amino groups to cause the polyamine to adhere to the carbon leaving pendant amine groups free to react further. The free amine groups are derivatized by treatment with a difunctional compound having amine reactive moieties, so that free amine groups of the enzyme can be covalently bound to the polyamine via the amine reactive compound.

STATEMENT OF THE INVENTION

This invention provides a method of preparing an immobilized enzyme conjugate which comprises the steps of: (a) contacting porous, granular, diatomaceous earth with a solution of a polyamine compound having pendant amine groups to cause the polyamine to attach itself to the diatomaceous earth; (b) removing the solvent and any unattached polyamine dispersed therein from contact with the diatomaceous earth and contacting the thus treated diatomaceous earth with a solution of an amine reactive material which is a multifunctional aldehyde, a multifunctional organic halide, a multifunctional anhydride, a multifunctional azo compound, a multifunctional isothiocyanate or a multifunctional isocyanate to cause one of the reactive groups to react with the pendant amine groups and leave a pendant amine reactive moiety available for further reaction; and (c) removing the solvent and any unreacted amine reactive material dissolved therein from contact with the diatomaceous earth support and contacting it with a solution of at least one enzyme to be immobilized to cause the amine groups of the enzyme(s) to react with the unreacted amine reactive moiety by the formation of covalent bonds therebetween thereby to immobilize the enzyme(s). Also included within the scope of the invention is an immobilized enzyme conjugate comprising porous, granular, diatomaceous earth having attached thereto the reaction product of a polyamine compound having pendant amine groups and an amine reactive material which is a multifunctional aldehyde, a multifunctional organic halide, a multifunctional anhydride, a multifunctional azo compound, a multifunctional isothiocyante or a multifunctional isocyanate whose unreacted amine reactive groups have been reacted with free amine groups of enzyme or enzymes to bind it thereto.

DESCRIPTION OF THE INVENTION

Any GDE (granular diatomaceous earth) may be used in the present invention. A very suitable GDE preferably has a particle size of from approximately −16 to +48 mesh on the U.S. sieve series. Pore dimensions will preferably range in radii from approximately 35 angstroms to 1000 angstroms, and surface area preferably ranges from approximately 20 to 60 m$^2$/gram.

The porous granular diatomaceous earth used in the Examples below (supplied by Eagle Pitcher Ind., Inc.) is fairly inexpensive and has good mechanical strength, and stability on exposure to heat and to acidic or basic solutions. Its physical and chemical properties are as follows:

| Physical Properties (Typical) | |
|---|---|
| Particle size | −16 to +48 mesh |
| Bulk density | 38 lbs./ft.$^3$ |
| | (575 kg/m$^3$) |
| Shape | Essentially spherical |
| Crushing strength | Approximately 250 psi |
| | (17.6 to 18.6 kg/cm$^2$) |
| Particles per pound (24/48 mesh) | 13 million |
| Particles per pound (16/24 mesh) | 1 million |
| Color | Light tan |
| Average Surface area | 40 m$^2$/gram |
| Average Pore volume | 0.16 ml/gram |
| Average Pore Diameter | 155 Angstrom |
| Chemical Properties (Approximate) | |
| Silica (SiO$_2$) | 90% |
| Alumina (Al$_2$O$_3$) | 6.5% |
| Iron Oxide (Fe$_2$O$_3$) | 2.3% |
| Lime (CaO) | 0.2% |
| Magnesia (MgO) | 0.3% |
| Other oxides | 0.3% |
| Ignition loss (in addition to moisture at 105°) | 0.4% |
| pH in solution | 6.5–7.0 |
| Moisture content | Less than 1.0% |
| Chemical Properties (Approximate) continued | |
| Structure | Predominantly amorphous diatomaceous earth |

Because of the chemical stability, physical toughness, and low cost, this porous GDE makes an excellent support for use in column reactors Specific examples of polyamines suitable for use in the present invention include polyethylenediamine, a polyethylenimine such as, for example, polydiethylenetriamine, polytriethylenetetramine, polypentaethylenehexamine or polyhexamethylenediamine. Also, Betz 1180 ® may be used. This is a water soluble copolymer of epihalohydrin and polyamine and is marketed by Betz Laboratories, Inc., Trevose, Pa. Other suitable polyamines are polymethylenedicyclohexylamine, polymethylenedianiline, polytetraethylenepentamine and polyphenylenediamine. While the molecular weight of the polyamine is not deemed critical, polymers with a molecular weight range of from 500 to 100,000 are preferred. Those polyamines which are water soluble are applied to the GDE from their aqueous solutions whereas non-water soluble polymers are applied from organic solvents. Suitable solvents include, but are not limited to, methyl alcohol, ethyl alcohol, propyl alcohol, isopropyl alcohol, t-butyl alcohol, acetone, methyl ether, ethyl ether, propyl ether, isopropyl ether, toluene, benzene, xylene, hexane, cyclopentane and cyclohexane.

While the exact mechanism is not known, it is believed that contacting the GDE with the polyamine solution, which will usually be of a concentration of approximately 1 to 100 gm of polyamine to liter of solvent, causes the polyamine to become attached to the surface and possibly entrapped in the pores of the GDE particle. Thus, while a portion of the polymer would be expected to be adsorbed to the surface of the GDE particle, a portion also would be expected to be attracted into the pores of the porous support so that the macromolecule projects out from the pore leaving the functional groups (amino groups) available for further reaction. The present method is in contrast to the prior method described in previously mentioned U.S. Pat. No. 3,796,634 in which carbon powder is treated with a solution of polyethylenimine to change its surface charge and thereby allow absorption of the enzyme to the modified carrier. This prior method depends on charge interaction which is much less desirable than the covalent linkages formed in the process of this invention. The treated GDE is removed from contact with the polyamine solution, such as by decantation or by filtration, and preferably washed with a solvent mentioned in the paragraph above, such as with deionized (DI) water, to remove any non-adhering polymer.

The polyamine treated GDE is next treated with a solution of a multifunctional amine reactive material such as glutaraldehyde; bis-diazobenzidine-2,2'-disulfonic acid; 4,4'-difluoro-3,3,'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate; toluene-2, -4-diisothiocyanate; diazobenzidine; diazobenzidine-3,3'-dianisidine; N,N'-hexamethylene bisiodoacetamide; hexamethylene diisocyanate; cyanuric chloride and 1,5-difluoro-2,4-dinitrobenzene by contacting it with a solution preferably containing from approximately 1 to 100 gm per liter of the amine reactive material. Those amine reactive materials which are water soluble are applied to the GDE from their aqueous solutions whereas non-water soluble polymers are applied from organic solvents. Suitable solvents include but are not limited to, methyl alcohol, ethyl alcohol, propyl alcohol, isopropyl alcohol, t-butyl alcohol, acetone, methyl ether, ethyl ether, propyl ether, isopropyl ether, toluene, benzene, xylene, hexane, cyclopentane and cyclohexane. After allowing the reaction to proceed for a time sufficient to permit the amine reactive material to derivatize the free amine groups of the polyamine, the treated GDE is removed from the solution of amine reactive material and preferably washed several times with deionized water. As used herein, the term "derivatize" is intended to represent the formation of a reaction product between the amino functional group of the polyamine molecule bound to the GDE and the pendant amine reactive moiety of the amine reactive material.

Any enzyme containing an amino group capable of reacting with the pendant amine reactive moiety can be immobilized by this method. Also, two or more enzymes can be coimmobilized. These enzymes include, for example, trypsin, papain, hexokinase, ficin, bromelin, lactic dehydrogenase, lactase, glucose isomerase, glucoamylase, chymotrypsin, pronase, acylase, invertase, beta amylase, alpha amylase, pullulanase, transglucosidase, glucose oxidase, pepsin, rennin and fungal protease. The derivatized GDE is mixed with a solution of the enzyme(s) to perfect the enzyme immobilization. The enzyme may be in an aqueous solution and/or a solvent compatible with the enzyme. The immobilization may be the batch type, or on an industrial scale, immobilization may be carried out in a columnar reactor. Removal of the GDE from the enzyme solution preferably with subsequent water washing provides the GDE immobilized enzyme suitable for use in biocatalytic conversions.

One of the unexpected observations of the enzyme immobilization method of this invention is that, in general, GDE immobilized enzymes are superior in the sense that they exhibit longer life and better thermostability than the carbon immobilized enzymes prepared according to U.S. Pat. No. 4,438,196. This property, which is very important when considering a heterogeneous biocatalyst is illustrated by the Examples which follow.

Another desirable feature of this immobilization process is that a previously used GDE support can be re-used for immobilization after regeneration by a simple process involving a base-acid wash. Typically, the used support is slurried in (1) water, (2) 0.5 N NaOH, (3) water, (4) 0.5 N HCl, and then (5) water. This property of the process is significant because it eliminates any disposal problem for the user and provides a potential economic savings as well.

Another desirable attribute resides in the embodiment involving coimmobilization of more than one enzyme, as is illustrated in Examples V and VI below.

Preferably, in practicing this invention, the diatomaceous earth particles are washed with water until clear and then suction deaerated. The polyamine, preferably polyethylenimine (Mol. Wt. 500–100,000) in an aqueous solution, is then added to the washed GDE, preferably in a ratio of approximately 10 ml GDE to approximately 50 ml polyethylenimine (PEI) aqueous solution. Concentrations between approximately 0.1%–0.5% (w/v) of PEI aqueous solution have been successfully used, and more preferably, approximately 0.15 to 0.20% (pH measured at 9.0–9.9) of PEI (Mol. Wt. 40,000–60,000) aqueous solution is added to the GDE. The effective reaction time can range between approximately 0.5 to 8 hours at approximately 20° to 30° C. with gentle agitation, with a reaction time of between approximately 2 to 5 hours at room temperature preferred. The excess PEI solution can be removed by decanting and washing the amine treated GDE with water. When glutaraldehyde is used as a crosslinking agent, it is typically added to the PEI treated GDE in approximately the same volume ratio as was the PEI. Glutaraldehyde concentrations of approximately 0.1 to 1.0% (w/v) are effective in this immobilization process. The preferred concentration is approximately 0.25–0.7% (w/v) aqueous glutaraldehyde solution containing 0.05 M sodium bicarbonate for a desired pH of approximately 7.9 to 8.3. Typically, the glutaraldehyde-bicarbonate solution has a measured pH of 8.2. The crosslinking reaction is carried out at approximately 20°–30° C. for approximately 0.5 to 20 hours, preferably for approximately 2 hours at room temperature with gentle agitation. Any excess glutaraldehyde solution can be removed by decanting and washing the treated GDE with water. Enzyme immobilization can be carried out at a temperature between approximately 4° and 30° C., at a pH suitable for the particular enzyme being immobilized, for approximately 1 to 10 hours with gentle agitation. The preferred conditions involve 4 hours of agitation at room temperature. The immobilized enzymes thus obtained can be stored in water or suitable buffer solution preferably in the cold in a refrigerator, more preferably at 1° to 10° C., and even more preferably 4° C., until used.

The catalyst support of the present invention has been found to be well suited to the immobilization of enzymes in general. Enzymes immobilized according to the present invention are substantially more thermally stable than solubilized enzymes or enzymes immobilized according to U.S. Pat. No. 4,438,196, and thus most importantly, the present invention is particularly suitable for use with heat-labile enzymes.

The immobilized enzyme activity per ml support can be varied and controlled by the particle sizes of support and the degree of loading of enzyme(s).

The immobilization procedure produces a linkage between the enzyme and the polymer absorbed to the granular diatomaceous earth that is unusually stable, and it has been found that the diatomaceous earth particle does not become coated and fouled by proteins or other substances when a crude solution of liquefied corn starch is passed through a bed of the immobilized enzyme.

The present invention is further illustrated by the following Examples in which all mesh sizes are based on the U.S. standard sieve series. The Examples are intended to illustrate the preferred embodiments and not limit the invention thereby.

Unless otherwise indicated in the Examples, the activity of the enzyme or enzymes, either immobilized or solubilized, was determined as follows. The assay was conducted at 50° C. using as a substrate 50 ml of 10% w/v Maltrin-150 (dextrose equivalent 10–12) corn starch obtained from Grain Processing Company, (Muscatine, Iowa) in 0.05 M acetate buffer at pH 4.2. To carry out the assay, the substrate and enzyme were placed in a shake flask and incubated for 30 minutes. The amount of glucose formed is estimated by the Glucostrate Method (General Diagnostics) whereby the initial rate (also called initial velocity) of glucose formed per minute is determined from regression analysis. One unit of enzyme activity represents the amount of enzyme which will produce 1 micromole of glucose (or glucose equivalent) in 1 minute under the conditions of each enzyme assay, and is reported in U/ml (units of activity per milliliter of support).

In the Examples, the amount of sugar formed was determined by the Ferricyanamide Method as described by Ghuysen, et al, in *Methods in Enzymology*, Volume VIII, page 685, Academic Press, N.Y. (1966) in which glucose was used as the reference.

EXAMPLE I

IMMOBILIZATION OF GLUCOAMYLASE ON PEI-DERIVATIZED POROUS GRANULAR DIATOMACEOUS EARTH

Prior to use for immobilization, the granular diatomaceous earth (GDE) was washed as follows:

1. 100 ml of −20 to +24 mesh (U.S. sieve) porous granular diatomaceous earth (Eagle Pitcher Industry, Inc.) was mixed with deionized water. Enough water was used to immerse the diatomaceous earth completely.
2. After the diatomaceous earth settled, the supernatant liquid was decanted.
3. The diatomaceous earth was then suction deaerated, and the residual water decanted.

Glucoamylase (AG) was immobilized at room temperature by the following procedure:

1. 500 ml of a 0.2% w/v aqueous solution of PEI-600 (Cordova Chemical Company, Muskegon, Mich., polyethylenimine molecular weight range 40,000-60,000) having a pH measured at 9.8 was added to the 100 ml sample of washed diatomaceous earth in a 1 liter erlenmeyer flask and gently shaken for 4 hours.
2. Excess polyethylenimine solution was then decanted and the treated diatomaceous earth washed with copious amounts of water.
3. The pendant amine groups of the polymer attached to the diatomaceous earth were derivatized with glutaraldehyde by the addition of 500 ml of a 0.5% w/v glutaraldehyde solution made up in 0.05 M sodium bicarbonate which resulted in a pH of 8.2. The flask was gently agitated for 2 hours at room temperature.
4. The glutaraldehyde solution was decanted and the treated diatomaceous earth washed with deionized water to remove unreacted glutaraldehyde. The result was a support comprising diatomaceous earth, polyethylenimine, and glutaraldehyde.
5. 500 ml of a solution containing 12,000 units glucoamylase (Diazyme® L-200, a trademark of Miles Laboratories, Inc., Elkhart, Ind.) adjusted to pH 7.0 with 0.02 M phosphate buffer was added to the derivatized support and gently agitated for 4 hours at room temperature.
6. The liquid was decanted and the immobilized enzyme was washed with deionized water.

The immobilized glucoamylase was found to contain 110 10 units of activity per ml of support.

Use of Granular Diatomaceous Earth Immobilized Glucoamylase to Produce High Dextrose Syrups A sample of 50 ml of the immobilized glucoamylase thus prepared was packed in a jacketed glass column of 2.5 cm diameter and 100 cm height. 30% enzyme liquefied starch (40 DE) (23.63% glucose, 10.99% maltose, 0% isomaltose; degree of polmerization: $DP_3$ 13.10%, $DP_4$ 7.10%, greater than $DP_4$ 45.18%), pH 4.2 buffered with 5 mM acetate, was fed continuously to the column at various flow rates. The temperature of the column was kept at 50° C. The products were analyzed by HPLC (high pressure liquid chromatography) and GC (gas chromatography). The results are given in the following table.

TABLE I

| Flow Rate (ml/hr) | Carbohydrate Composition (%) | | | | | |
|---|---|---|---|---|---|---|
| | Glucose | Maltose | Iso-maltose | $DP_3$ | $DP_4$ | $>DP_4$ |
| 25.4 | 94.3 | 1.1 | 0.8 | 0.4 | 0 | 3.5 |
| 13.3 | 95.7 | 1.3 | 1.5 | 0.4 | 0 | 1.2 |
| 11.0 | 96.6 | 1.1 | 1.8 | 0.3 | 0 | 0.2 |
| 9.1 | 94.1 | 1.4 | 3.8 | 0.7 | 0 | Trace |

*Maltose component contained small amounts of unidentified $DP_2$ sugars.

Thus, a maximum glucose level as high as 96.6% can be reached verifying that a dextrose level similar to soluble glucoamylase saccharification can be obtained. This high level of dextrose at 30% DS indicates that the enzyme is at or very near the surface of the particle such that internal diffusion is not a major factor influencing the reaction. Also, the high sugar fraction ($>DP_3$) is able to be easily hydrolyzed by the immobilized enzyme, further indicating little steric hindernace or the easy access of the substrate to the enzyme active site.

EXAMPLE II

Granular Diatomaceous Earth Immobilized Glucoamylase As Compared to Carbon Immobilized Glucoamylase Thermostability:

Thermostability tests of soluble glucoamylase, carbon immobilized glucoamylase according to Example I of U.S. Pat. No. 4,438,196, and GDE immobilized glucoamylase prepared as in Example I above were conducted at 60° C. and pH 4.2 (0.1 M acetate buffer) in the absence of substrate. The results are shown in Table II-A.

TABLE II-A (Percent activity of glucoamylase remaining after incubation for the specified time at 60° C. and pH 6.0)

| Time (minutes) | % Activity Remaining | | | |
|---|---|---|---|---|
| | 30 | 60 | 120 | 180 |
| Soluble | 82.6 | 73.2 | 66.4 | 54.7 |
| Carbon Immobilized | 87.0 | 72.4 | 54.7 | 51.4 |
| GDE Immobilized | 91.6 | 78.7 | 72.6 | 64.2 |

As shown in the Table, immobilization of glucoamylase on porous granular diatomaceous earth resulted in an improvement in enzyme thermostability.

Stability and Productivity:

One liter of immobilized glucoamylase prepared as in Example I above was packed in a jacketed glass column (5 cm × 100 cm). The column was run continuously at 50° C., feeding as the substrate 30% DS (dry solids) dual enzyme liquefied cornstarch (35 DE) at pH 4.2 buffered with 2.5 mM acetate and containing 250 ppm $SO_2$. Also, the substrate had been stored cold at 5° C. and then was passed through a small 70° C. column filled with plain granular diatomaceous earth to act as a check filter prior to entering the enzyme column. The glucose levels in the products were in a range between 94% to 96%. The half-life for this column was about 125 days with a productivity of about 153 grams DS per ml immobilized glucoamylase.

For comparison, carbon immobilized glucoamylase prepared in accordance with Example I of U.S. Pat. No. 4,438,196 was tested in a column the same manner as described in the paragraph above (except the DS was 25%). Although the lower DS favors a more complete conversion of the available starch and thus the yield should be better, the glucose levels in the products were in a range between 92% to 93%. The half-life for this column was about 67 days with a productivity of about 107 grams DS per ml immobilized glucoamylase.

The results of the carbohydrate profile at various flow rates through each column are summarized in Table II-B below.

TABLE II-B

| Flow rate (Bed Volume/Hr.)* | CARBOHYDRATE PROFILE (%) | | | | |
|---|---|---|---|---|---|
| | $DP_1$ | Maltose and $DP_2$ | Isomaltose | $DP_3$ | $>DP_3$ |
| AG bound to GDE. | | | | | |
| Substrate | 21.8 | 8.7 | 0 | 11.5 | 58.0 |
| 1.5 | 89.6 | 1.3 | 0.5 | 0.4 | 8.2 |
| 1.0 | 92.6 | 1.5 | 0.8 | 0.4 | 4.7 |
| 0.8 | 94.4 | 1.3 | 1.0 | 0.3 | 3.0 |
| 0.6 | 95.2 | 1.4 | 1.3 | 0.3 | 1.8 |
| 0.5 | 95.1 | 1.4 | 1.6 | 0.3 | 1.6 |
| 0.4 | 95.9 | 1.4 | 2.0 | 0.3 | 0.4 |
| 0.3 | 95.1 | 1.5 | 2.5 | 0.3 | 0.6 |
| 0.2 | 93.6 | 1.6 | 3.6 | 0.8 | 0.4 |
| AG bound to granular carbon. | | | | | |
| Substrate | 1.6 | 5.9 | 0 | 12.1 | 80.4 |
| 2.0 | 84.2 | 1.6 | 0.2 | 0.7 | 13.3 |
| 1.6 | 85.6 | 1.3 | 0.3 | 0.6 | 12.2 |
| 1.0 | 88.5 | 1.3 | 0.5 | 0.4 | 9.3 |
| 0.8 | 92.5 | 1.4 | 0.7 | 0.4 | 5.0 |
| 0.5 | 91.7 | 1.3 | 1.0 | 0.2 | 5.8 |
| 0.3 | 92.7 | 1.5 | 1.6 | 0.1 | 4.1 |
| 0.2 | 93.9 | 1.6 | 2.4 | 0.1 | 2.0 |
| 0.1 | 92.7 | 1.9 | 4.3 | 0.4 | 0.7 |
| 0.05 | 92.6 | 1.9 | 4.8 | 0.3 | 0.4 |

*Bed volume/hour is a flow rate value that is inversely related to the reaction time.

From Table II-B it can be determined that glucoamylase bound to GDE is capable of hydrolyzing starch more completely than glucoamylase bound to granular carbon. Maximum dextrose of about 96% is reached by glucoamylase bound to GDE and about a 95% level with glucoamylase bound to carbon. The increased dextrose yield may indicate that the AG bound to GDE is less sterically hindered or is bound more at the surface of the particle so that the substrate experiences less diffusion resistance. Another indication of less diffusion resistance with glucoamylase bound to GDE is the lower level of isomaltose formed at the respective dextrose level.

EXAMPLE III

Immobilization of glucoamylase was repeated in the same manner as in Example I with variation of the particle size of the GDE, and of the amounts of glucoamylase immobilized to compare the activity of the glucoamylase to the amount of the glucoamylase.

The data reported in the Table below shows the effect of particle size and enzyme loading amount have on the activity of the enzyme support composite using glucoamylase as a model system.

TABLE III

| Granular Diatomaceous Earth (Mesh Size) | Loading Amounts of Glucoamylase Presented to Support (U/ml Support) | Activity of Glucoamylase Support Composite (U/ml Support) | Recovery of Immobilized Enzyme (%) |
|---|---|---|---|
| −16 to +24 | 70.0 | 51.6 | 73.7 |
| −16 to +24 | 140.0 | 116.3 | 83.1 |
| −16 to +24 | 200.0 | 178.8 | 89.4 |
| −16 to +24 | 400.0 | 196.5 | 49.1 |
| −16 to +24 | 800.0 | 189.6 | 23.7 |
| −16 to +24 | 1200.0 | 191.1 | 15.9 |
| −24 to +48 | 70.0 | 69.6 | 99.4 |
| −24 to +48 | 140.0 | 135.5 | 96.8 |
| −24 to +48 | 260.0 | 234.3 | 90.1 |
| −24 to +48 | 400.0 | 294.5 | 73.6 |
| −24 to +48 | 800.0 | 295.2 | 36.9 |
| −24 to +48 | 1200.0 | 299.9 | 25.0 |

From Table III it can be determined that as the loading amount increases so does the activity until the loading amount reaches approximately 200 units/ml for the −16 to +24 mesh particle size, and 300 for the −24 to +48 mesh particle size, and then the activity levels off.

EXAMPLE IV A 100 ml quantity of PEI-glutaraldehyde derivatized GDE as in Example I (but made with −24 to +48 mesh GDE) was used to immobilize soy beta-amylase (Hi-maltosin S, Hankyu Kyoei Bussan Co., Ltd., Osaka, Japan). The enzyme solution used for treating the derivatized GDE was 1 gram ( 40,000 units/gram) of the soy beta-amylase in 500 ml of 0.02 M phosphate buffer at pH 7.0. The immobilization procedure was carried out as in Example I. The immobilized beta-amylase thus obtained was assayed (pH 5.5) at 134 units per ml support.

Use of Granular Diatomaceous Earth Immobilized Beta-Amylase to Produce High Maltose Syrups Samples of 50 ml each of 30% DS Maltrin-150 (Grain Processing Corp.) in 0.05 M acetate solution at pH 5.0 were digested in shake flasks for 24 hours at 50° C. with various amounts of immobilized beta-amylase thus prepared in order to produce high maltose syrups. The products were analyzed for carbohydrate composition by HPLC. The results are given in the following Table.

TABLE IV-A

| Immobilized β-amylase (ml) | Carbohydrate Composition (%) | | | |
|---|---|---|---|---|
| | $DP_1$ | $DP_2$ | $DP_3$ | $>DP_3$ |
| 0 | 1.2 | 3.5 | 2.8 | 92.5 |
| 0.2 | 1.2 | 37.0 | 11.2 | 50.6 |
| 0.4 | 1.2 | 42.4 | 12.7 | 43.7 |
| 0.9 | 1.1 | 47.2 | 12.8 | 38.9 |
| 1.8 | 1.1 | 51.8 | 12.7 | 34.3 |
| 3.5 | 1.2 | 53.8 | 12.7 | 32.4 |
| 7.0 | 1.1 | 55.2 | 12.4 | 31.3 |

From Table IV-A it can be determined that a maximum dextrose level of approximately 55% can be achieved.

Thermostability of Granular Diatomaceous Earth Immobilized Beta-Amylase

Thermostability tests of soluble β-amylase, carbon immobilized β-amylase prepared according to Example IV of U.S. Pat. No. 4,438,196, and the presently prepared β-amylase bound to GDE were carried out at 60° C. in acetate buffer (0.1M, pH 5.5) in the absence of substrate. The results are shown in Table IV-B.

TABLE IV-B (Percent activity of beta-amylase remaining after incubation at 60° C. and pH 6.0)

| Time (minutes) | Remaining Activity (%) | | | |
|---|---|---|---|---|
| | 30 | 60 | 120 | 180 |
| Soluble | 87.2 | 17.2 | 4.7 | 1.4 |
| Carbon Immobilized | 84.2 | 58.6 | 46.0 | 43.2 |
| GDE Immobilized | 100 | 100 | 91.5 | 86.6 |

The thermal stability of the β-amylase bound to GDE was dramatically increased. After 1 hour, essentially no loss in activity was observed for the GDE immobilized enzyme, but less than 60% of the carbon immobilized enzyme activity and less than 20% of the soluble enzyme activity remained. Even after three hours at 60° C. over 85% of the GDE immobilized β-amylase was still active compared to less than 45% of the carbon immobilized enzyme and less than 5% for the soluble enzyme.

EXAMPLE V

Preparation of Coimmobilized Glucoamylase/Pullulanase

A 100 ml quantity of derivatized GDE as in Example I (but made with −24 to +48 mesh) was used for the immobilization. The derivatized GDE was treated with 500 ml of a pH 6.0 buffer solution (0.1 M acetate) containing 12,000 units of glucoamylase (Diazyme L-200, Miles Laboratories, Inc.) and 12,000 units of pullulanase (Promozyme® 200L, Novo Ind., Inc.), by which the enzymes were coimmobilized on the porous GDE support by the method described in Example I. The coimmobilized glucoamylase-pullulanase composite thus obtained was assayed at 54.5 units/ml glucoamylase activity and 12.3 units/ml pullulanase activity using 1% (w/v) pullulan as substrate.

Use of Coimmobilized Glucoamylase/Pullulanase Composite to Produce High Dextrose Syrups High dextrose syrups were prepared by digesting 50 ml samples of 30% DS enzyme liquified cornstarch (40 DE) in 0.05 M acetate at pH 4.2 in shake flasks for 24 hours at 50° C. with various amounts of coimmobilized glucoamylase-pullulanase composite thus prepared. The carbohydrate profiles are given in the following Table.

TABLE V

| Coimmobilized Glucoamylase-Pullulanase (ml) | CARBOHYDRATE COMPOSITION* (%) | | | | |
|---|---|---|---|---|---|
| | $DP_1$ | Maltose** | Isomaltose | $DP_3$ | $>DP_3$ |
| Substrate | 18.2 | 12.7 | 0 | 23.4 | 45.7 |
| 1.7 | 68.7 | 20.7 | 0.1 | 2.3 | 8.2 |
| 3.5 | 95.1 | 2.3 | 0.2 | 1.9 | 0.5 |
| 5.2 | 95.9 | 1.5 | 0.4 | 1.3 | 1.1 |
| 6.9 | 96.6 | 1.3 | 0.4 | 0.6 | 1.1 |
| 8.7 | 97.3 | 1.3 | 0.5 | 0.5 | 0.5 |

*Composition determined from both HPLC and GC.
**Maltose component contains small amounts of unidentified $DP_2$ sugars.

The syrups thus obtained are higher in glucose and lower in isomaltose than those obtained in Example I. A combination of glucoamylase/pullulanase has a different hydrolysis profile from glucoamylase by itself, theoretically due to the combined action of glucoamylase and pullulanase.

EXAMPLE VI

Preparation of Coimmobilized Beta-Amylase/Pullulanase

A 100 ml quantity of derivatized porous GDE as in Example I (but made with −24 to +48 mesh GDE) was used for immobilization. A solution was prepared by mixing one gram beta-amylase (Hi-Maltosin S) and 20 ml of pullulanase (Pulluzyme ®750L, ABM Chemicals Limited of Woodley Stockport Cheshire, England) in 0.005 M acetate buffer at pH 5.5. The beta-amylase and pullulanase were then coimmobilized on the porous GDE by the method given in Example I.

Use of Granular Diatomaceous Earth Coimmobilized Beta-Amylase/Pullulanase to Produce High Maltose Syrups The high maltose syrups were produced by hydrolyzing 50 ml samples of 30% DS Maltrin-150 in 0.05 M acetate at pH 5.5 in shake flasks for 24 hours at 50° C. with various amounts of coimmobilized beta-amylase/pullulanase thus prepared. The HPLC sugar profiles of the products are given in the following Table.

TABLE VI

| Coimmobilized Beta-Amylase/ Pullulanase (ml) | HPLC Sugar Profile (%) | | | |
|---|---|---|---|---|
| | $DP_1$ | $DP_2$ | $DP_3$ | $>DP_3$ |
| 0 | 1.2 | 3.5 | 2.8 | 92.5 |
| 0.4 | 2.8 | 46.9 | 15.2 | 35.1 |
| 0.9 | 2.8 | 53.1 | 13.3 | 30.8 |
| 1.8 | 2.8 | 57.9 | 13.4 | 25.9 |
| 3.5 | 2.9 | 62.6 | 14.1 | 20.5 |
| 7.0 | 3.0 | 67.3 | 13.3 | 16.4 |

The results indicate that compositions of the high maltose syrup prepared by coimmobilized beta-amylase/pullulanase are better than those produced by immobilized beta-amylase alone (Example IV), i.e., higher in maltose and lower in higher molecular weight sugars. As in Example V, this is theoretically attributed to the combined action of Beta-amylase and pullulanase.

EXAMPLE VII

A 100 ml quantity of PEI-glutaraldehyde derivatized GDE as in Example I (but made with −24 to +48 mesh GDE) was used to immobilize pullulanase (Pulluzyme 750L). 500 ml of 0.05 M acetate at pH 5.5 containing 24 ml of the enzyme were used for treating the derivatized GDE. The immobilization procedure was carried out as in Example I. The immobilized pullulanase thus obtained was assayed (pH 6.0) at 32 units per ml support.

Thermostability of Immobilized Pullulanase

Thermostability tests of soluble pullulanase and the thus prepared pullulanase bound to GDE were conducted at 60° C. and pH 6.0 (0.1 M acetate) in the absence of substrate. The results are shown in Table VII.

TABLE VII (Percent activity of pullulanase remaining after incubation for the specified time at 60° C. and pH 6.0)

| Time (minutes) | Activity Remaining (%) | | | |
|---|---|---|---|---|
| | 30 | 60 | 120 | 180 |
| Soluble | 19.7 | 6.0 | 0 | 0 |
| GDE Immobilized | 51.4 | 42.2 | 42.2 | 38.4 |

As seen in Table VII, the immobilized pullulanase was significantly more thermally stable than the soluble enzyme. After 0.5 hour, GDE immobilized pullulanase still retained over 50% activity where the soluble pullulanase was already below 20% activity. By 2 hours, GDE immobilized pullulanase still retained around 42% activity but soluble pullulanase had already gone down to 0% activity.

EXAMPLE VIII

Preparation of Immobilized Lactase

A 100 ml quantity of PEI-glutaraldehyde derivatized GDE as in Example I (but made with −24 to +35 mesh) was used to immobilize lactase. One gram of lactase (20,000 units) from *A. oryzae* was dissolved in 500 ml of 0.02 M sodium phosphate buffer solution (pH 7.0) and immobilized to GDE by the same method given in Example I. Lactase activity was assayed at 50° C. and pH 4.5 using 5% (w/v) lactose as substrate. The released glucose was determined by the glucostrate method. One unit lactase activity is defined as the amount of enzyme which produced one micromole of glucose per minute at 50° C. at pH 4.5. The immobilized lactase thus obtained was assayed at 106.7 units per ml support.

Use of Granular Diatomaceous Earth Immobilized Lactase to Hydrolyze Lactose

Hydrolysis of 50 ml sample of 15% (w/v) lactose (0.05 M sodium acetate pH 4.5) with immobilized lactase bound to GDE was conducted in shake flasks for 24 hours at 50° C. The HPLC sugar profiles of the hydrolyzed products are given in the following Table.

TABLE VIII-A

| Immobilized Lactase (ml) | HPLC Sugar Profile (%) | | | | |
|---|---|---|---|---|---|
| | Glucose | Galactose | Lactose | DP$_3$ | DP$_4$ |
| 0 | — | — | 100.0 | — | — |
| 0.9 | 34.4 | 25.4 | 31.2 | 7.3 | 1.7 |
| 1.8 | 42.6 | 37.1 | 16.6 | 3.3 | 0.4 |
| 3.5 | 47.2 | 45.0 | 5.2 | 1.6 | — |
| 5.2 | 48.6 | 47.7 | 2.9 | 0.8 | — |
| 7.0 | 48.8 | 48.3 | 2.4 | 0.5 | — |
| 10.4 | 48.9 | 48.5 | 2.6 | — | — |

The degree of lactose hydrolysis was over 97% indicating that the immobilized lactase bound to GDE was rather active.

Thermostability of Immobilized Lactase

Thermostability tests of soluble lactase and the thus prepared lactase bound to porous GDE were conducted at 60° C. and pH 4.5 (0.1 M sodium acetate) in the absence of substrate. The results are shown in table VIII-B.

TABLE VIII-B (Percent activity of lactase remaining after incubation for the specified time at 60° C. and pH 4.5)

| Time (minutes) | Activity Remaining (%) | | | |
|---|---|---|---|---|
| | 30 | 60 | 120 | 180 |
| Soluble | 52.4 | 32.4 | 16.8 | 10.0 |
| GDE Immobilized | 76.0 | 72.6 | 61.6 | 53.4 |

EXAMPLE IX

Preparation of Immobilized Transglucosidase

A 100 ml quantity of PEI-glutaraldehyde derivatized GDE as in Example I (but made with −24 to +48 mesh) was used to immobilize transglucosidase. 500 ml of 0.05 M acetate at pH 5.5 containing 500 units of a purified thermal stable transglucosidase from *Talaromyces duponti* were used. The immobilization was carried out by the same method given in Example I. The immobilized transglucosidase thus obtained was assayed 2.6 units per ml support. Transglucosidase activity was assayed by a method based on the liquid chromatography quantitative measurement of a transglucosylic product, namely panose in an incubation mixture of enzyme and maltose at pH 4.5 and 60° C. One unit of transglucosidase activity is defined as the amount of enzyme which produced one micromole of panose per hour from 20% maltose solution at pH 4.5 and 60° C.

Use of Granular Diatomaceous Earth Immobilized Transglucosidase to Produce Non-Fermentable Sugars Non-fermentable sugars (mainly panose and isomaltose) were produced by digesting 50 ml of 30% DS maltose solution (pH 4.5, 0.05 M acetate) in a shake flask with 10 ml of immobilized transglucosidase thus prepared for five days at 60° C. GC analysis of the product showed the following sugar profile: 28.3% glucose, 34.8% maltose, 7.4% isomaltose, 22.1% panose and 7.5% higher sugars. The total amount of non-fermentable sugars ($\alpha$1-6 linkage) produced in this Example was about 37%.

What is claimed is:

1. A method of preparing an immobilized enzyme conjugate which comprises the steps of:
   (a) contacting porous, granular, diatomaceous earth with a solution of a polyamine compound having pendant amine groups to cause the polyamine to attach itself to the diatomaceous earth;
   (b) removing the solvent and any unattached polyamine dispersed therein from contact with the diatomaceous earth and contacting the thus treated diatomaceous earth with a solution of an amine reactive material which is a multifunctional aldehyde, a multifunctional organic halide, a multifunctional anhydride, a multifunctional azo compound, a multifunctional isothiocyanate or a multifunctional isocyanate to cause one of the reactive groups to react with the pendant amine groups and leave an amine reactive moiety available for further reaction;
   (c) removing the solvent and any unreacted amine reactive material dissolved therein from contact with the diatomaceous earth support and contacting it with a solution of at least one enzyme to be immobilized to cause the amine groups of the enzyme or enzymes to react with the unreacted amine reactive moiety by the formation of covalent bonds therebetween thereby to immobilize the enzyme or enzymes.

2. The method of claim 1 wherein the polyamine is selected from the group consisting of polyethylenediamine, a polyethylenimine, polyhexamethylenediamine, polymethylenedicyclohexylamine, polymethylenedianiline, polytetraethylenepentamine, polyphenylenediamine, and a copolymer of epihalohydrin and polyamine.

3. The method of claim 2 wherein the polyethylenimine is polydiethylenetriamine, polytriethylenetetramine, polypentaethylene-hexamine or polyhexamethylenediamine.

4. The method of claim 1 wherein the polyamine has a molecular weight range of from 500 to 100,000.

5. The method of claim 1 wherein the amine reactive material is bis-diazobenzidine-2,-2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate, toluene-2,4-diisothiocyanate, diazobenzidine; diazobenzidine-3,3'-dianisidine; N,N'-hexamethylene bisiodoacetamide; hexamethylene diisocyanate; cyanuric chloride; 1,5-difluoro-2,4-dinitrobenzene; or glutaraldehyde.

6. The method of claim 2 wherein the amine reactive material is glutaraldehyde.

7. The method of claim 1 wherein the enzyme is glucoamylase, beta-amylase, pullulanase, transglucosidase, lactase, trypsin, papain, hexokinase, ficin, bromelin, lactic dehydrogenase, glucose isomerase, chymotrypsin, pronase, acylase, invertase, alpha amylase, glucose oxidase, pepsin, rennin, fungal protease, or a mixture thereof.

8. The method of claim 7, wherein the diatomaceous earth has a particle size from approximately −16 to +48 mesh on the U.S. sieve series, pore dimensions from approximately 35 angstroms to 1,000 angstroms in radius, and a surface area from approximately 20 to 60 m$^2$/gram.

9. An immobilized enzyme conjugate comprising porous, granular, diatomaceous earth having attached thereto the reaction product of a polyamine compound having pendant amine groups, an amine reactive material which is a multifunctional aldehyde, a multifunctional organic halide, a multifunctional anhydride, a multifunctional azo compound, a multifunctional isothiocyanate or a multifunctional isocyanate whose unreacted amine reactive groups have been reacted with free amine groups of enzyme or enzymes to bind it thereto.

10. The conjugate of claim 9 wherein the diatomaceous earth has a particle size of from approximately −16 to +48 mesh on the U.S. sieve series, pore dimensions of from approximately 35 to 1,000 angstroms in radius and a surface area of from approximately 20 to 60 m$^2$/gram, and the polyamine is selected from the group consisting of polyethylenediamine, a polyethylenimine, polyhexa- methylenediamine, polymethylenedicyclohexylamine, polymethylenedianiline, polytetraethylenepentamine, polyphenylenediamine, and a copolymer of epihalohydrin and a polyamine.

11. The conjugate of claim 10 wherein the polyethylenimine is polydiethylenetriamine, polytriethylenetetramine, polypentaethylene-hexamine polyhexamethylenediamine, or a copolymer of epihalohydrin and a polyamine.

12. The conjugate of claim 9 wherein the polyamine has a molecular weight of from 500 to 100,000.

13. The conjugate of claim 9 wherein the amine reactive material is bis-diazobenzidine-2,2'-disulfonic acid; 4,4'-difluoro-3,3'-dinitrodiphenylsulfone; diphenyl-4,4'-dithiocyanate-2,2'-disulfonic acid; 3-methoxydiphenylmethane-4,4'-diisocyanate; toluene-2-isocyanate-4-isothiocyanate, toluene-2,4-diisothiocyanate; diazobenzidine; diazobenzidine-3,3'-dianisidine; N,N'-hexamethylene bisiodoacetamide; hexamethylene diisocyanate; cyanuric chloride; 1,5-difluoro-2,4-dinitrobenzene; or glutaraldehyde.

14. The conjugate of claim 10 wherein the amine reactive material is glutaraldehyde.

15. The method of claim 9 wherein the enzyme is glucoamylase, beta-amylase, pullulanase, transglucosidase, lactase, trypsin, papain, hexokinase, ficin, bromelin, lactic dehydrogenase, glucose isomerase, chymotrypsin, pronase, acylase, invertase, alpha amylase, glucose oxidase, pepsin, rennin, fungal protease, or a mixture thereof.

16. A method of preparing an immobilized enzyme conjugate, and saccharifying starch therewith, which comprises the steps of:
(a) contacting porous, granular, diatomaceous earth with a solution of a polyamine compound having pendant amine groups to cause the polyamine to attach itself to the diatomaceous earth;
(b) removing the solvent and any unattached polyamine dispersed therein from contact with the diatomaceous earth and contacting it with a solution of an amine reactive material which is a multifunctional aldehyde, a multifunctional organic halide, a multifunctional anhydride, a multifunctional azo compound, a multifunctional isothiocyanate or a multifunctional isocyanate to cause one of the amine reactive groups to react with the pendant amine groups and leave an amine reactive moiety available for further reaction;
(c) removing the solvent and any unreacted amine reactive material dissolved therein from contact with the diatomaceous earth support and contacting it with a solution of the enzyme or enzymes to be immobilized to cause the amine groups thereof to react with the unreacted amine reactive moiety by the formation of covalent bonds therebetween thereby to immobilize the glucoamylase; and
(d) contacting the immobilized enzyme or enzymes with liquid starch thereby to accomplish the saccharification of the starch.

17. The method of claim 16 wherein the enzyme is glucoamylase, beta-amylase, pullulanase, alpha amylase, or a mixture thereof.

18. The method of claim 17 wherein the diatomaceous earth has an average pore volume of approximately 0.16 ml/gram, an average pore diameter of approximately 155 angstroms, and an average surface area of approximately 40 m$^2$/gram.

19. The method of claim 18 wherein after sufficient starch has been saccharified to wholly or partially inactive the enzyme or enzymes, the bed or column of immobilized enzyme or enzymes is washed with water, dilute sodium hydroxide, dilute hydrochloric acid or a mixture thereof thereby to restore the granular, activated diatomaceous earth support for reuse.

* * * * *